United States Patent [19]

Pilgram et al.

[11] 4,166,735

[45] Sep. 4, 1979

[54] CYCLOALKANECARBOXANILIDE DERIVATIVE HERBICIDES

[75] Inventors: Kurt H. G. Pilgram; Richard D. Skiles, both of Modesto, Calif.

[73] Assignee: Shell Oil Company, Houston, Tex.

[21] Appl. No.: 876,595

[22] Filed: Feb. 10, 1978

Related U.S. Application Data

[63] Continuation-in-part of Ser. No. 761,515, Jan. 21, 1977, abandoned.

[51] Int. Cl.² .................... C07C 103/19; A01N 9/12; A01N 9/14; A01N 9/20
[52] U.S. Cl. .......................... 71/118; 71/98; 71/103; 260/556 B; 260/557 R; 260/562 P
[58] Field of Search ............ 260/556 B, 557 R, 562 P; 71/98, 103, 118

[56] References Cited

U.S. PATENT DOCUMENTS

| | | | |
|---|---|---|---|
| 3,211,544 | 10/1965 | Dubrovin | 71/118 |
| 3,328,156 | 6/1967 | Hopkins | 71/118 |
| 3,407,056 | 10/1968 | Schwartz | 71/118 |
| 3,484,485 | 12/1969 | Schwartz | 260/557 R |
| 3,660,486 | 5/1972 | Thiele | 260/562 P |
| 3,753,679 | 8/1973 | Singhal | 71/98 |
| 4,090,865 | 5/1978 | Baker | 260/562 P X |

FOREIGN PATENT DOCUMENTS

| | | | |
|---|---|---|---|
| 749581 | 10/1970 | Belgium | 71/118 |
| 1921840 | 11/1969 | Fed. Rep. of Germany | 260/562 P |
| 1141183 | 1/1969 | United Kingdom | 260/557 R |
| 1246885 | 9/1971 | United Kingdom | 260/557 R |
| 1255161 | 12/1971 | United Kingdom | 260/557 R |
| 1344735 | 1/1974 | United Kingdom | 71/98 |

OTHER PUBLICATIONS

Martin et al., CA 74: 12853w (1971).
Esso, CA 79: 18343e (1973).

*Primary Examiner*—Thomas A. Waltz

[57] ABSTRACT

Certain cycloalkanecarboxanilide derivatives are useful as herbicides.

8 Claims, No Drawings

CYCLOALKANECARBOXANILIDE DERIVATIVE HERBICIDES

CROSS-REFERENCE TO RELATED APPLICATIONS

This application is a continuation-in-part of Ser. No. 761,515, filed Jan. 21, 1977, now abandoned.

BACKGROUND OF THE INVENTION

1. Field of the Invention

This invention related to cycloalkanecarboxanilide derivatives, their use as herbicides and to herbicidal compositions containing these cycloalkanecarboxanilides.

SUMMARY OF THE INVENTION

The present invention is directed to a new class of compounds which are useful to control plant growth. This class of compounds is characterized as amides derived from a substituted cycloalkanecarboxylic acid and certain 3,4-disubstituted anilines.

DETAILED DESCRIPTION OF THE INVENTION

The present invention is directed to new compounds, particularly useful as herbicides, having the formula

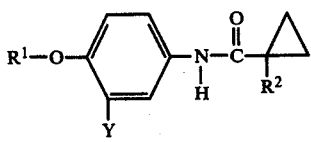

wherein
Y is a halogen atom of atomic number 9 to 35, inclusive, $NO_2$ or the group -$Z_p$-alkyl in which the alkyl portion contains from 1 to 6 carbon atoms and can be substituted by one or more halogen atoms of atomic number 9 to 35, inclusive;
Z is O, S, SO or $SO_2$;
$R^1$ is an alkyl group of from 1 to 6 carbon atoms, an alkenyl group of from 2 to 6 carbon atoms or an aryl group of from 6 to 10 carbon atoms, each optionally substituted by one or more halogen atoms having an atomic number of from 9 to 35, inclusive, or is an alkynyl group of from 3 to 4 carbon atoms, an alkoxyalkyl group in which each alkyl group contains from 1 to 6 carbon atoms, a cycloalkyl or (cycloalkyl)alkyl group having from 3 to 7 carbon atoms in the ring, an aralkyl group of from 7 to 9 carbon atoms optionally ring-substituted by one or two halogen atoms having an atomic number of 9 to 35, inclusive, or by alkyl of from 1 to 4 carbon atoms;
$R^2$ is an alkyl group of from 1 to 6 carbon atoms, a halogen atom having an atomic number of 9 to 35, inclusive or an alkoxy group in which the alkyl portion contains from 1 to 6 carbon atoms; with the proviso that when Y is $NO_2$ then $R^1$ is other than methyl; and
p is 0 or 1.

The compounds shown in formula I above are derivatives of substituted-cyclopropane carboxylic acids. Examples where $R^2$ in the formula is alkyl include methyl, ethyl, propyl, n-butyl and the like or where $R^2$ is a halogen atom, fluorine, chlorine or bromine. $R^2$ can also be methoxy or lower alkyl homologs.

As a general rule, the compounds preferred because of their herbicidal properties are those compounds of formula I wherein $R^2$ is methyl. The compounds wherein $R^2$ is chlorine are also very active. Compounds wherein $R^2$ is methoxy are also desirable.

The group Y can be chlorine, bromine or fluorine, $NO_2$, trifluoromethyl, trifluoromethoxy, methyl, ethyl, methylsulfonyl, trifluoromethylsulfonyl and the like.

Preferred because of their herbicidal properties are compounds of formula I wherein Y is trifluoromethyl. Compounds wherein Y is methyl, ethyl, chlorine, bromine or $NO_2$ are also very active.

$R^1$ can be straight- or, preferably branched-chain alkyl such as methyl, ethyl, isopropyl, isobutyl, secondary-butyl, tertiary-butyl, isoamyl and the like, 2-chloroethyl, trifluoromethyl, allyl, phenyl, p-chlorophenyl, naphthyl, propargyl, cyclopropyl, cyclohexyl, methylcyclopropyl, cyclopropylmethyl and the like. Additionally, $R^1$ can be such groups as 2-methoxyethyl, benzyl, phenethyl, p-chlorobenzyl or o-methylbenzyl.

Compounds wherein $R^1$ is alkyl of 1 to 4 carbon atoms or cycloalkyl are generally preferred. Especially active are those compounds wherein $R^1$ is branched chain alkyl such as isopropyl or tert-butyl and the like. Ethyl, methyl and 1-cyclopropylethyl derivatives and ring alkylated forms are also highly active. Variations in activity of course depend on the individual combinations of $R^1$, $R^2$ and Y.

Examples of species contemplated within the scope of the invention include:
4'-(isopropoxy)-3'-(trifluoromethyl)-1-propylcyclopropanecarboxanilide
4'-(isoamyloxy)-3'-nitro-1-butylcyclopropanecarboxanilide
4'-(isopropoxy)-3'-methyl-1-fluorocyclopropanecarboxanilide Examples of species contemplated when Y is trifluoromethyl include the following:
4'-(isobutoxy)-3'-(trifluoromethyl)-1-methylcyclopropanecarboxanilide
4'-(isoamyloxy)-3'-(trifluoromethyl)-1-propylcyclopropanecarboxanilide
4'-(2-fluorobenzyloxy)-3'-(trifluoromethyl)-1-methylcyclopropanecarboxanilide
4'-(2-chlorobenzyloxy)-3'-(trifluoromethyl)-1-butylcyclopropanecarboxanilide
4'-(4-chlorobenzyloxy)-3'-(trifluoromethyl)-1-methylcyclopropanecarboxanilide
4'-(2,6-dichlorobenzyloxy)-3'-(trifluoromethyl)-1-ethylcyclopropanecarboxanilide
4'-(propargyloxy)-3'-(trifluoromethyl)-1-methylcyclopropanecarboxanilide
4'-(sec-butoxy)-3'-(trifluoromethyl)-1-propylcyclopropanecarboxanilide Preferred because of their herbicidal properties are compounds of formula I wherein $R^2$ is methyl and $R^1$ is alkyl of 1 to 4 carbon atoms, cyclopropylmethyl or 1-cyclopropylethyl. The alkyl group is preferably branched-chain such as sec-butyl, or isopropyl. Haloalkyl such as 2-chloroethyl is also desirable.

Compounds of formula I wherein Y is $NO_2$ are a useful subclass of the invention due to their relative easy and low cost of preparation as well as to their herbicidal properties.

Examples of species contemplated where Y is $NO_2$ include the following:

4'-((2-propyloxy)ethoxy)-3'-nitro-1-ethylcyclopropanecarboxanilide

4'-(isobutoxy)-3'-nitro-1-butylcyclopropanecarboxanilide

4'-(ethoxy)-3'-nitro-1-propylcyclopropanecarboxanilide

4'-(allyloxy)-3'-nitro-1-ethylcyclopropanecarboxanilide

4'-(2,6-dichlorobenzyloxy)-3'-nitro-1-propylcyclopropanecarboxanilide

Preferred because of their herbicidal properties are those compounds where Y is $NO_2$ and $R^1$ is alkyl of 2 to 4 carbon atoms. Especially useful compounds appear to be those wherein $R^1$ is isopropyl as these compounds show useful crop selectivities.

Examples of species contemplated when Y is alkyl include the following:

4'-(cyclopropylmethoxy)-3'-methyl-1-methylcyclopropanecarboxanilide

4'-(1-cyclopropylethoxy)-3'-methyl-1-methylcyclopropanecarboxanilide

4'-(1-methylpropoxy)-3'-methyl-1-methylcyclopropanecarboxanilide

4'-(ethoxy)-3'-ethyl-1-methylcyclopropanecarboxanilide

4'-(methoxy)-3'-ethyl-1-methylcyclopropanecarboxanilide

4'-(methoxy)-3'-ethyl-1-chlorocyclopropanecarboxanilide

4'-(isopropoxy)-3'-methyl-1-methylcyclopropanecarboxanilide

4'-(isopropoxy)-3'-methyl-1-chlorocyclopropanecarboxanilide

4'-(methoxy)-3'-isopropyl-1-methylcyclopropanecarboxanilide

4'-(isopropoxy)-3'-methyl-1-bromocyclopropanecarboxanilide

4'-(tert-butoxy)-3'-methyl-1-methylcyclopropanecarboxanilide

4'-(1-methylcyclopropoxy)-3'-methyl-1-methylcyclopropanecarboxanilide

4'-methoxy-3'-(sec-butyl)-1-methylcyclopropanecarboxanilide

Examples of species contemplated when Y is halogen include the following:

4'-(isobutoxy)-3'-bromo-1-methylcyclopropanecarboxanilide

4'-(isopropoxy)-3'-bromo-1-methylcyclopropanecarboxanilide

4'-(tert-butoxy)-3'-bromo-1-methylcyclopropanecarboxanilide

The corresponding chloro and fluoro derivatives are also examples of compounds contemplated by the invention as well as the following compounds:

4'-methoxy-3'-chloro-1-methylcyclopropanecarboxanilide

4'-ethoxy-3'-chloro-1-methylcyclopropanecarboxanilide

4'-(isopropoxy)-3'-fluoro-1-methylcyclopropanecarboxanilide

4'-(isopropoxy)-3'-chloro-1-methylcyclopropanecarboxanilide

4'-ethoxy-3'-fluoro-1-methylcyclopropanecarboxanilide

4'-(isobutoxy)-3'-fluoro-1-methylcyclopropanecarboxanilide

4'-(sec-butoxy)-3'-fluoro-1-methylcyclopropanecarboxanilide

Of course, the corresponding bromo derivatives can also be used.

Cycloalkylcarboxanilides, I, can be prepared according to the following sequence of reactions:

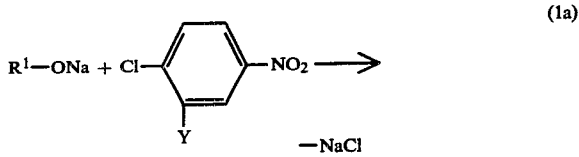

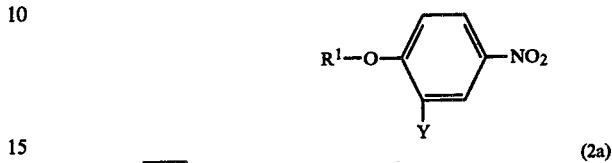

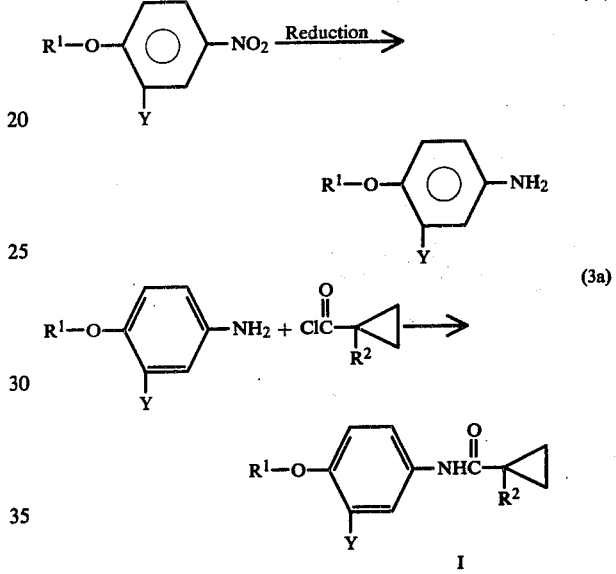

The appropriate sodium alkoxide is allowed to react with 3-substituted-4-chloronitrobenzene to give 3,4-disubstituted nitrobenzene; step (1a). In step (2a) the 3,4-disubstituted nitrobenzene is reduced to give the corresponding aniline. In step (3a) the aniline and a cycloalkylcarboxylic chloride are allowed to react to give the desired cycloalkylcarboxanilide, I.

Reaction (1a) is readily conducted by mixing the reactants in a solvent such as an alcohol, dimethyl sulfoxide or dimethylformamide at room temperature or at a moderately elevated temperature, for example up to 150° C.

The reduction of the 3,4-disubstituted nitrobenzenes, step (2a) is readily carried out in boiling water containing iron filings and up to 5% of acetic or hydrochloric acid. However, any of numerous reduction techniques that reduce an aromatic nitro group to amino are applicable here (see R. Schröter and F. Möller in Methoden der Organische Chemie. "Houben-Weyl", Vol. 11, 1, part IV, p. 341–731, Georg Thiene Verlag, Stuttgart (1957)).

The acylation reaction (3a) is conducted by treating the 3,4-disubstituted aniline with a cycloalkylcarboxylic chloride in a suitable solvent such as ether, tetrahydrofuran, benzene, toluene or hexane in the presence of one molar equivalent of an organic or inorganic base that can serve as acceptor for the hydrogen chloride formed in the reaction. Organic bases such as tertiary amines (pyridine, triethylamine, collidine, N,N-dimethylaniline, ethyldiisopropylamine) or inorganic bases ($Na_2$-

$CO_3$, $NaHCO_3$, $K_2CO_3$, $CaCO_3$) may be used to trap the hydrogen chloride formed during acylation.

The cycloalkylcarboxylic chlorides used in the reaction or simple esters from which they can be generated are generally known in the art as for example in U.S. Pat. Nos. 3,277,171, 3,211,544 and South African application 64/1283. The 1-fluorocycloalkylcarboxylic chlorides can be readily prepared by treating 1-chlorocycloalkylcarboxylic acid ethyl ester with potassium fluoride at elevated temperatures optionally in the presence of solvents and/or phase transfer catalysts and converting the ester to acid chloride in a known manner. The 1-bromocycloalkylcarboxylic chlorides can be prepared by bromination of cycloalkylcarboxylic chlorides under refluxing conditions in a nitrogen atmosphere.

The compounds of the invention, for example, 4'-(isopropoxy)-3'-bromo-1-methylcyclopropanecarboxanilide, 4'-(isopropoxy)-3'-(trifluoromethyl)-1-methylcyclopropanecarboxanilide and 4'-(isopropoxy)-3'-(ethyl)-1-methylcyclopropanecarboxanilide have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of Formula I. Likewise the invention also includes a method of controlling plant growth which comprises applying to the locus an effective amount of a compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w or appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of all compounds, intermediates and final, were confirmed by elemental analysis, and infrared and nuclear magnetic spectral analyses. The examples are for the purpose of illustration only and should not be regarded as limiting the invention in any way.

EXAMPLE 1

4'-Isopropoxy-3'-(trifluoromethyl)-1-methylcyclopropanecarboxanilide (a) Preparation of 3-(trifluoromethyl)-4-isopropoxynitrobenzene To a chilled (5° C.) solution of 118 g (0.5 mole) of 3-(trifluoromethyl)-4-chloronitrobenzene in 100 ml of dimethyl sulfoxide (DMSO) was added dropwise a solution containing 41 g (0.5 mole) of sodium isopropoxide in 300 ml of dimethyl sulfoxide. The dark reaction mixture was stirred at ambient temperature for one hour, poured into water and extracted with ether. The ether extracts were washed with water, dried and concentrated. Recrystallization of the residual liquid from hexane gave 115.5 g (92.7%) of white crystalline solid; m.p. 34°–36°.

(b) Preparation of 3-(trifluoromethyl)-4-isopropoxyaniline

To a refluxing mixture containing 113.3 g (0.455 mole) of (1a) in 1200 ml of 5% aqueous acetic acid and 50 ml of methanol was added portionwise with stirring 137.5 g of iron filings. The reaction mixture was refluxed for one hour, filtered while hot, cooled and extracted with ether. The ether extracts were dried and concentrated to give 72.3 g (72.6%) of product as an amber oil.

(c) Preparation of 4'-isopropoxy-3'-(trifluoromethyl)-1-methylcyclopropanecarboxanilide To a stirred solution containing 10.9 g (0.05 mole) of (1b) and 5.0 g (0.05 mole) of triethylamine in 100 ml of tetrahydrofuran was added dropwise 5.9 g (0.05 mole) of 1-methylcyclopropanecarboxylic chloride. This addition was exothermic to 55°. The reaction mixture was stirred and refluxed for 30 minutes, and concentrated under reduced pressure. The resulting solid was washed with water, dried and recrystallized from ether to give 14.5 g (97%) of white crystalline solid; m.p. 106°–109° C.

EXAMPLE 2

4'-(Benzyloxy)-3'-trifluoromethyl-1-methylcyclopropanecarboxanilide (a) Preparation of 3-(trifluoromethyl)-4-(benzyloxy)nitrobenzene To a solution containing 45.1 g (0.02 mole) of 3-(trifluoromethyl)-4-chloronitrobenzene in 100 ml of DMSO was added dropwise at ambient temperature a solution containing 26 g (0.2 mole) of sodium benzyloxide in 75 ml of benzyl alcohol causing the temperature to rise 40° C. After 48 hours at ambient temperature, the reaction mixture was poured into ice water and extracted with ether, and the extract was dried and concentrated to about 200 ml. To the concentrated solution was added 200 ml of hexane and the resulting solution was cooled. Filtration gave 51.5 g (87%) of colorless crystalline solid; m.p. 112°–114° C.

(b) Preparation of 3-(trifluoromethyl)-4-(benzyloxy)aniline

To a refluxing mixture containing 64.5 g (0.217 mole) of (2a) in 700 ml of 5% aqueous acetic acid and 30 ml of methanol was added portionwise within 15 minutes 65.5 g of iron filings. The mixture was stirred and refluxed for an additional 30 minutes, filtered while hot, cooled and extracted with ether. The ether extract was washed with water, dried and concentrated to give 56.0 g (97%) of product as a light-amber oil that crystallized on standing.

(c) Preparation of 4'-(benzyloxy)-3'-(trifluoromethyl)-1-methylcyclopropanecarboxanilide To a solution of 2.7 g (0.01 mole) of (2b) and 2.7 g (0.01 mole) of triethylamine in 50 ml of tetrahydrofuran was added with stirring at ambient temperature 1.2 g (0.01 mole) of 1-methylcyclopropanecarboxylic acid chloride. After one hour, the reaction mixture was poured into ice water and extracted with 200 ml of ether. The ether extract was dried and concentrated. Recrystallization of the residual solid from ether gave 3.6 g of product, m.p. 120°–122° C.

EXAMPLE 3

4'-(Cyclopropylmethoxy)-3'-(trifluoromethyl)-1-methylcyclopropanecarboxanilide (a) Preparation of 3-(trifluoromethyl)-4-(cyclopropylmethoxy)nitrobenzene To a cooled (10° C.) solution containing 22.5 g (0.1 mole) of 3-(trifluoromethyl)-4-chloronitrobenzene in 100 ml of DMSO was added with stirring at ambient temperature a solution containing 0.11 mole of sodium cyclopropylmethoxide (prepared by dissolving 4.9 g of 57% sodium hydride in 7.9 g of cyclopropylmethanol and 50 ml of tetrahydrofuran) in 100 ml of DMSO. The reaction mixture was heated at 50° C. for one hour, poured into ice water and filtered. Recrystallization of the filter cake from hexane gave 11.0 g (42%) of product as a white crystalline solid, m.p. 41°–44° C.

(b) Preparation of 3-(trifluoromethyl)-4-(cyclopropylmethoxy)aniline

To a stirring and refluxing mixture containing 11.0 g (0.042 mole) of (3a) in 150 ml of 5% aqueous acetic acid was added 28 g of iron filings and 10 ml of methanol. The mixture was refluxed and stirred vigorously for one hour, then extracted with ether after cooling. The ether extract was washed with aqueous sodium bicarbonate, dried, and concentrated to give 9.5 g (98%) of product as an amber oil.

(c) Preparation of 4'-(cyclopropylmethoxy)-3'-(trifluoromethyl)-1-methylcyclopropanecarboxanilide To a solution of 4.6 g (0.02 mole) of (3b) and 2.0 g (0.02 mole) of triethylamine in 30 ml of tetrahydrofuran was added 2.4 g (0.02 mole) of 1-methylcyclopropanecarbonyl chloride. The mixture was refluxed for one hour, poured into ice water, and extracted with ether. The extract was dried and concentrated, and the residue was recrystallized from hexane to give 5.0 g (79%) of white crystalline solid; m.p. 84°–85° C.

EXAMPLE 4

4'-(4-Chlorophenoxy)-3'-(trifluoromethyl)-1-methylcyclopropanecarboxanilide (a) Preparation of 4-(4-chlorophenoxy)-3-(trifluoromethyl)nitrobenzene To a solution containing 64.2 g (0.5 mole) of 4-chlorophenol and 112.7 g (0.5 mole) of 2-chloro-5-nitrobenzotrifluoride in 400 ml of DMSO was added dropwise with stirring at 30°–35° C. a solution containing 20 g (0.5 mole) of sodium hydroxide in 20 ml of water. After 1.5 hours, the reaction mixture was poured into cold water and extracted with 800 ml of ether. The ether solution was dried and concentrated under reduced pressure to give 158 g (99%) of product that crystallized on standing; melting point, 46°–48° C. (from hexane).

(b) Preparation of 4-(4-chlorophenoxy)-3-(trifluoromethyl)aniline

To a refluxing mixture containing 156 g (0.492 mole) of the nitro compound prepared as in (a) above in 1180 ml of 5% aqueous acetic acid was added portionwise 140 g of powdered iron. After 2 hours, the reaction mixture was filtered through filter aid and the residue was washed with methanol. The combined filtrates were extracted with 7×300 ml of ether. The combined ether extracts were washed with aqueous sodium bicarbonate, dried and concentrated to give 141.5 g of product; melting point, 43°–45° C. (from hexane).

(c) Preparation of 4'-(4-chlorophenoxy)-3'-(trifluoromethyl)-1-methylcyclopropanecarboxanilide To a stirred solution of 5.75 g (0.02 mole) of the amine prepared under (b) above in 40 ml of tetrahydrofuran was added dropwise 2.4 g (0.02 mole) of 1-methylcyclopropylcarboxylic chloride. The mixture was stirred and heated at 60° C. for 0.5 hour, poured into ice water and filtered. The filter cake was recrystallized from ether-hexane (1:3) to give 6.5 g (88%) of product, m.p. 115°–117° C.

EXAMPLE 5

4'-(4-Chlorophenoxy)-3'-(trifluoromethyl)-1-butylcyclopropanecarboxanilide

To a solution containing 2.9 g (0.01 mole) of the amine prepared in Example 4 (b), and 1.0 g (0.01 mole) of triethylamine in 50 ml of tetrahydrofuran was added dropwise 1.7 g (0.01 mole) of 1-butylcyclopropanecarboxylic acid chloride. The mixture was stirred and heated at 60° C. for 0.5 hour, poured into ice water and extracted with ether. The ether extract was dried and concentrated under reduced pressure. The residual yellow syrup was crystallized from hexane to give 3.3 g (80%) of product as a tan solid, m.p. 104°–106° C.

EXAMPLES 6–15

In the manner described above, and illustrated in foregoing Examples, additional cyclopropanecarboxanilides listed in Table 1 were prepared.

Table 1

Cyclopropanecarboxanilides

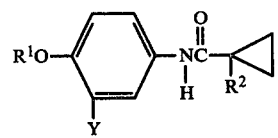

| Example | Y | $R^1$ | $R^2$ | % Yield | M.P., °C |
|---|---|---|---|---|---|
| 6 | $CF_3$ | $CH_3-$ | $CH_3$ | 96 | 106–108 |
| 7 | $CF_3$ | $C_2H_5-$ | $CH_3$ | 98 | 83–85 |
| 8 | $CF_3$ | $CH_3OCH_2CH_2-$ | $CH_3$ | 98 | 83–85 |
| 9 | $CF_3$ | $CH_2=CHCH_2-$ | $CH_3$ | 89 | 58–60 |
| 10 | $CF_3$ | $C_2H_5CH(CH_3)-$ | $CH_3$ | 89 | 93–95 |
| 11 | $CF_3$ | $(CH_3)_2CHCH_2-$ | $CH_3$ | 95 | 91–93 |
| 12 | $CF_3$ | $CH_3(CH_2)_3-$ | $CH_3$ | 72 | 68–70 |
| 13 | $CF_3$ | $(CH_3)_2CH-$ | $C_2H_5$ | 59 | 89–90 |
| 14 | $CF_3$ | $ClCH_2CH-$ | $CH_3$ | 97 | 83–86 |
| 15 | $NO_2$ | $(CH_3)_2CH-$ | $CH_3$ | 47 | 100–101 |

EXAMPLE 16

4'-(Cyclopropylmethoxy)-3'-chloro-1-methylcyclopropanecarboxanilide (a) Preparation of 3-chloro-4-(cyclopropylmethoxy)nitro benzene To a solution containing 38.4 g of 3,4-dichloronitrobenzene in 150 ml of DMSO was added 17.3 g of cyclopropylmethanol. This solution was stirred during the dropwise addition of 9.2 g of sodium hydroxide dissolved in 10 ml of water. This addition was exothermic to 45° C. The mixture was stirred and heated to 75°–80° for 18 hours, than poured over ice water and filtered. The filter cake was recrystallized from methanol to yield 27 g (59%) of light tan solid, melting point, 42°–44° C.

(b) Preparation of a 3-chloro-4-(cyclopropylmethoxy)aniline

To a heated mixture containing 26.7 g of (a) in 300 ml of 5% aqueous acetic acid was added 56 g of iron filings and 15 ml of methanol. The mixture was refluxed and stirred vigorously for one hour. The mixture was filtered while hot and the cooled filtrate was extracted with ether. The ether extract was washed with aqueous sodium bicarbonate, dried, and concentrated to give 22.8 g (99%) of product, melting point, 54°–55° C.

(c) Preparation of 4'-(cyclopropylmethoxy)-3'-chloro-1-methylcyclopropanecarboxanilide To a solution of 4.9 g of (b) and 2.5 g of triethylamine in 50 ml of tetrahydrofuran was added dropwise 3.0 g of 1-methylcyclopropanecarboxylic acid chloride. The mixture was refluxed for 30 minutes, poured into ice water, and filtered, and the filter cake was recrystallized from methanol/water (4:1) to give 6.5 g (93%) of white crystalline solid, m.p. 111°–113° C.

EXAMPLES 17–24

In the manner described in the above Example, additional cyclopropanecarboxanilides listed in Table 2 were prepared.

Table 2
Cyclopropanecarboxanilides

| Ex. | $R^1$ | % Yield | Melting Point, °C. |
|---|---|---|---|
| 17 | phenyl-CH$_2$— | 89 | 107–109 |
| 18 | (2-chlorophenyl)-CH$_2$— | 86 | 146–149 |
| 19 | (3,4-dichlorophenyl)-CH$_2$— | 80 | 135–137 |
| 20 | (2,6-dichlorophenyl)-CH$_2$— | 95 | 150–152 |
| 21 | CH$_3$OC$_2$H$_2$— | 75 | 74–75 |
| 22 | (CH$_3$)$_2$CH— | 67 | 107–110 |
| 23 | CH$_3$— | 92 | 128–130 |
| 24 | cyclopropyl-CH(CH$_3$)— | 87 | 87–89 |

EXAMPLE 25

4'-(Isopropoxy)-3'-(trifluoromethyl)-1-chlorocyclopropanecarboxanilide

To a solution of 10.95 g 1 (b) in 100 ml of tetrahydrofuran and 5.05 g of triethylamine was added dropwise at ambient temperature 6.95 g of 1-chlorocyclopropanecarboxylic chloride. The reaction mixture was allowed to stand for two days, then concentrated to dryness. The resulting solid was washed with water and recrystallized from 80% aqueous methanol to give 10 g (62%) of white solid; m.p. 106°–108° C.

EXAMPLE 26

4'-(Isopropoxy)-3'-methyl-1-methylcyclopropanecarboxanilide (a) Preparation of isopropyl ortho-tolyl ether To a solution of 54.1 g (0.5 mole) of ortho-cresol in 150 ml of DMSO was added portionwise and with stirring 12 g of 57% sodium hydroxide. This addition was exothermic to 45° C. After 2 hours at ambient temperature, 61.5 g (0.5 mole) of isopropyl bromide in 50 ml of DMSO was added dropwise with stirring. After another 2 hours, the reaction mixture was poured into 1000 ml of ice water and extracted with ether. Distillation of the dried extract gave 53.9 g of product as a colorless liquid; b.p. 94°–96° C. (30 mm).

(b) Preparation of 2-isopropoxy-5-nitrotoluene

To a chilled (6° C.) solution containing 31.8 g (0.2 mole) of the ether prepared as in (a) above and 28.7 g of acetic anhydride in 200 ml of glacial acetic acid was added dropwise a solution of 13.9 g (0.22 mole) of 90% nitric acid in 100 ml of glacial acetic acid. The reaction mixture was allowed to stand at ambient temperature for 12 hours, poured into water and extracted with methylene chloride. The extract was washed with 5% sodium carbonate, water, dried, and concentrated to give 21.8 g of product as an amber oil.

(c) Preparation of 4'-(isopropoxy)-3'-methyl-1-methylcyclopropanecarboxanilide

A Parr shaker was charged with 21.8 g (0.11 mole) of (b) above and 2 g of 10% palladium-charcoal catalyst in 150 ml of tetrahydrofuran. The glass cylinder was pressurized with hydrogen (40 pounds) and shaken until hydrogen uptake ceased. The catalyst was removed by filtration. To the resulting solution was added 11.2 g of triethylamine and 12.6 g of 1-methylcyclopropanecarboxylic chloride. This addition was exothermic to 35° C. After 1 hour, the reaction mixture was concentrated to dryness and washed with water. Purification by silica chromatography gave 0.8 g of white crystaline solid; m.p. 99°–101° C.

EXAMPLE 27

4'-(Isopropoxy)-3'-chloro-1-methoxycyclopropanecarboxanilide

A mixture consisting of 5.6 g of 3-chloro-4-isopropoxyaniline, 3.9 g of methyl 1-methoxycyclopropanecarboxylate and 1.8 g of sodium methoxide in 50 ml of benzene was refluxed for 3 hours. The reaction mixture was concentrated to a volume of 25 ml, poured over ice water, acidified with hydrochloric acid and extracted with ether. The extract was dried, filtered and concentrated. Purification by silica chromatography gave 1.8 g of product as a white crystalline solid; m.p. 86°–87° C.

EXAMPLES 28–42

In the manner described for the above examples, additional cyclopropanecarboxanilides listed in Table 3 were prepared.

EXAMPLE OF HERBICIDAL ACTIVITY

The pre-emergence herbicidal activity of the compounds of the invention was evaluated by planting seeds of garden cress, downey brome, wild mustard (or sicklepod) and velvet leaf in test tubes, nominally measuring 25×200 millimeters, containing soil treated with the test compound at the rates of 0.1 and 1 mg per tube designated in Table I at Rates I and II, respectively. The planted soil was held under controlled conditions of temperature, moisture, and light for 13 to 14 days. The amount of germination and growth in each tube were evaluated on a 0 to 9 scale, 0 rating indicating no effect, 9 death of the seedlings or no germination.

The post-emergence activity of the compounds of this invention was evaluated by spraying 7-day old crabgrass plants, 10-day old pigweed plants, 7-day old downey brome plants, 10-day old wild mustard (or 7-day old sicklepod) and 10-day old velvet leaf plants to runoff with a liquid formulation of the test compound at the rates of 0.62 milliliter of an 0.05% solution designated Rate I in Table I, and 0.56 milliliter of an 0.5% solution designated Rate II in Table I. The sprayed plants were held under controlled conditions for 10 to 11 days and the effect of the test compound was then evaluated visually, the results being rated on the 0 to 9 scale described above.

The results of the pre- and post-emergence tests are summarized in Table I.

Table 3

Cyclopropanecarboxanilides

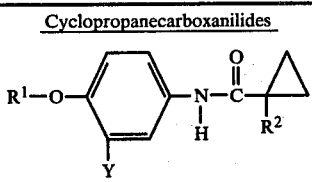

| Ex. | Y | $R^1$ | $R^2$ | % Yield | Melting Point, °C. |
|---|---|---|---|---|---|
| 28 | $CF_3$ | $C_2H_5-$ | Cl | 82 | 85–87 |
| 29 | Cl | (cyclopropyl)$CH(CH_3)-$ | Cl | 67 | 51–52 |
| 30 | Cl | (cyclopropyl)$CH_2-$ | Cl | 67 | 70–72 |
| 31 | Cl | $CH_3-$ | Cl | 76 | 95–98 |
| 32 | $CF_3$ | $Cl(CH_2)_2-$ | Cl | 100 | oil |
| 33 | Br | $(CH_3)_2CH-$ | $CH_3$ | 32 | 99–101 |
| 34 | $SCH_3$ | $C_2H_5-$ | $CH_3$ | 1 | 114–116 |
| 35 | $C_2H_5$ | $(CH_3)_2CH-$ | $CH_3$ | 11 | 120–121 |
| 36 | Br | (cyclopropyl)$CH(CH_3)-$ | $CH_3$ | 58 | 92–93 |
| 37 | Br | $CH_3-$ | $CH_3$ | 41 | 148–149 |
| 38 | Br | $C_2H_5-$ | $CH_3$ | 55 | 133.5–134.5 |
| 39 | $CH_3$ | $CH_3-$ | $CH_3$ | 68 | 134–135 |
| 40 | sec-butyl | $(CH_3)_2CH-$ | $CH_3$ | 26 | 85–86 |
| 41 | $C_2H_5$ | $CH_3-$ | $CH_3$ | 40 | 122–123 |
| 42 | $C_2H_5$ | $C_2H_5-$ | $CH_3$ | 25 | 87–89 |
| 43 | $CH_3$ | $C_2H_5-$ | $CH_3$ | 67 | — |
| 44 | $CH_3$ | $n-C_3H_7-$ | $CH_3$ | 39 | 94–96 |
| 45 | $C_2H_5$ | $n-C_3H_7-$ | $CH_3$ | 39 | 102–104 |
| 46 | $n-C_3H_7$ | $n-C_3H_7-$ | $CH_3$ | 28 | 67–69 |

TABLE I
RESULTS OF THE HERBICIDE ACTIVITY SCREEN

| | PRE-EMERGENCE (SOIL) | | | | | | | | POST-EMERGENCE (FOLIAR) | | | | | | | |
|---|---|---|---|---|---|---|---|---|---|---|---|---|---|---|---|---|
| | Garden Cress | | Downey Brome | | Wild Mustard | | Velvet Leaf | | Crabgrass | | Pigweed | | Downey Brome | | Wild Mustard | | Velvet Leaf |
| Example | I | II | I | II | I | II | I | II | I | II | I | II | I | II | I | II | I | II |
| 6 | 9 | 9 | 3 | 7 | 9 | 9 | 6 | 9 | 7 | 9 | 8 | 9 | 4 | 9 | — | — | 5 | 9 |
| 7 | 7 | 7 | 4 | 5 | 8 | 9 | 4 | 8 | 7 | 7 | 9 | 9 | 7 | 8 | 7 | 9 | 6 | 9 |
| 1 | 8 | 8 | 0 | 2 | 9 | 9 | 0 | 1 | 8 | 9 | 7 | 9 | 8 | 9 | 8 | 9 | 9 | 9 |
| 8 | 6 | 9 | 1 | 4 | 9 | 9 | 4 | 8 | 0 | 2 | 0 | 7 | 0 | 2 | 1 | 9 | 2 | 7 |
| 2 | 0 | 8 | 0 | 0 | 0 | 2 | 0 | 0 | 8 | 9 | 7 | 8 | 3 | 3 | 9 | 9 | 3 | 9 |
| 3 | 7 | 8 | 0 | 0 | 6 | 8 | 0 | 0 | 7 | 7 | 4 | 8 | 7 | 7 | 8 | 9 | 6 | 9 |
| 9 | 8 | 9 | 0 | 0 | 4 | 8 | 0 | 0 | 3 | 7 | 2 | 9 | 6 | 6 | 8 | 8 | 7 | 9 |
| 11 | 0 | 8 | 0 | 0 | 0 | 0 | 0 | 0 | 3 | 6 | 3 | 8 | 4 | 6 | 7 | 9 | 9 | 9 |
| 10 | 0 | 8 | 0 | 0 | 0 | 9 | 0 | 0 | 7 | 8 | 8 | 9 | 0 | 8 | 8 | 9 | 9 | 9 |
| 12 | 0 | 4 | 0 | 0 | 0 | 0 | 0 | 0 | 5 | 6 | 0 | 2 | 2 | 7 | 8 | 8 | 7 | 8 |
| 22 | — | — | 0 | 0 | 0 | 0 | 0 | 0 | 5 | 6 | 0 | 2 | 2 | 7 | 8 | 8 | 7 | 8 |
| 15 | 8 | 9 | 5 | 8 | 9 | 9 | 8 | 9 | 5 | 8 | 6 | 9 | 5 | 8 | 6 | 9 | 8 | 9 |
| 19 | 0 | 0 | — | — | — | — | — | — | 6 | 8 | 8 | 9 | — | — | — | — | — | — |
| 20 | 0 | 0 | — | — | — | — | — | — | 7 | 7 | 6 | 9 | — | — | — | — | — | — |
| 16 | 7 | 8 | 0 | 0 | 6 | 8 | 0 | 0 | 7 | 7 | 4 | 8 | 7 | 7 | 8 | 9 | 6 | 9 |
| 18 | 0 | 0 | — | — | — | — | — | — | 7 | 7 | 8 | 8 | — | — | — | — | — | — |
| 17 | 6 | 6 | — | — | — | — | — | — | 7 | 7 | 8 | 9 | — | — | — | — | — | — |
| 21 | 9 | — | — | — | — | — | — | — | 0 | 4 | — | — | — | — | — | — | — | — |

TABLE I-continued

| | 9 | — | — | — | 7 | 5 | — | — | — |

| | PRE-EMERGENCE (SOIL) | | | | | | | | POST-EMERGENCE (FOLIAR) | | | | | | | | |
|---|---|---|---|---|---|---|---|---|---|---|---|---|---|---|---|---|---|
| | Garden Cress | | Downey Brome | | Sicklepod | | Velvet Leaf | | Crabgrass | | Pigweed | | Downey Brome | | Sicklepod | | Velvet Leaf | |
| Example | I | II | I | II | I | II | I | II | I | II | I | II | I | II | I | II | I | II |
| 29 | 1 | 5 | 0 | 0 | — | — | 0 | 0 | 1 | 4 | 3 | 9 | 0 | 4 | — | — | 6 | 8 |
| 30 | 6 | 7 | 0 | 0 | — | — | 0 | 0 | 5 | 7 | 4 | 9 | 5 | 7 | — | — | 3 | 8 |
| 31 | 7 | 9 | 0 | 0 | — | — | 0 | 7 | 2 | 7 | 2 | 8 | 0 | 7 | — | — | 3 | 9 |
| 13 | 7 | 7 | 0 | 0 | — | — | 0 | 0 | 3 | 3 | 0 | 8 | 0 | 3 | — | — | 3 | 6 |
| 23 | 8 | 8 | 4 | 8 | — | — | 7 | 9 | 2 | 3 | 1 | 7 | 0 | 4 | — | — | 5 | 8 |
| 24 | 8 | 9 | 0 | 4 | — | — | 3 | 8 | 3 | 9 | 9 | 9 | 7 | 8 | — | — | 9 | 9 |
| 28 | 0 | 0 | 0 | 0 | — | — | 0 | 0 | 0 | 5 | 4 | 6 | 0 | 7 | — | — | 1 | 5 |
| 35 | — | — | 0 | 3 | — | — | 8 | 8 | 9 | 9 | 9 | 9 | 4 | 4 | 9 | 9 | 9 | 9 |
| 36 | — | — | 0 | 3 | — | — | 0 | 3 | 9 | 9 | 9 | 9 | 3 | 8 | 6 | 9 | 7 | 9 |
| 37 | 8 | 8 | 7 | 9 | 7 | 7 | 7 | 8 | 5 | 7 | 4 | 9 | 6 | 6 | 7 | 9 | 8 | 9 |
| 38 | 7 | 8 | 8 | 8 | 5 | 7 | 7 | 9 | 8 | 8 | 9 | 9 | 4 | 9 | 9 | 9 | 8 | 9 |
| 39 | 0 | 0 | 0 | 0 | 0 | 0 | 0 | 0 | 0 | 2 | 2 | 3 | 0 | 3 | 0 | 3 | 0 | 4 |
| 40 | 7 | 8 | 7 | 7 | 7 | 7 | 8 | 8 | 6 | 9 | 9 | 9 | 9 | 9 | 8 | 9 | 9 | 9 |
| 41 | 4 | 7 | 4 | 4 | 5 | 7 | 4 | 8 | 6 | 8 | 5 | 9 | 8 | 8 | 8 | 9 | 9 | 9 |
| 42 | 9 | 9 | 3 | 7 | 4 | 9 | 7 | 9 | 6 | 8 | 9 | 9 | 5 | 6 | 9 | 9 | 6 | 9 |

The herbicidal activity of the compounds of this invention was further determined with respect to several common species of weeds, by spraying a formulation of the test compound on the soil in which the weed seeds had been planted (pre-emergence test) or onto the foliage of the plants (post-emergence test). In each series of tests, the plants were grown in narrow trays and sprayed with chemical. The solution of the test compound was sprayed over the tray, from one end to the other, the concentration of the test compound in the formulation varying logarithmically from a higher value at one end of the band to a lower value at the other end of the band. The effect of the test compound was evaluated visually and reported as the nominal rate of application, in pounds of test compound per acre of the soil band, at which 90% inhibition of the growth of the weeds occurred, this being referred to as the 90% growth inhibition, or $GI_{90}$, dosage. Results of the pre-emergence and post-emergence tests, as well as the weed species involved, are set out in Tables II and III.

Table II

Results of Post-Emergence Foliar Application
Herbicide Rate Evaluation Screen
$GI_{90}$

| Ex. | Yellow-Foxtail | Fall-Panicum | Crab-grass | Pig-weed | Mustard | Velvet Leaf | Downey Brome | Barn-yard grass |
|---|---|---|---|---|---|---|---|---|
| 6 | 0.32 | 1.0 | 0.7 | 0.4 | 0.4 | >2.0 | — | — |
| 7 | <0.2 | 0.84 | <0.2 | <0.2 | 0.24 | — | — | — |
| | | 0.52 | | | | | | |
| 1 | <0.2 | 0.52 | <0.2 | <0.2 | <0.2 | <0.2 | — | — |
| 2 | 200 | >2.0 | >2.0 | <0.2 | <0.2 | >2.0 | — | — |
| 3 | <0.2 | 1.0 | 0.3 | 0.3 | <0.2 | 0.48 | — | — |
| 9 | 1.0 | 1.64 | 1.5 | 1.34 | 0.52 | 2.0 | >2.0 | 2.0 |
| 11 | 2.0 | 1.34 | >2.0 | 2.0 | 0.22 | 0.44 | >2.0 | >2.0 |
| 10 | 0.84 | 1.34 | 1.0 | 0.92 | 0.22 | 0.3 | 2.0 | 1.6 |
| 12 | >2.0 | >2.0 | >2.0 | 1.34 | <0.22 | 1.0 | >2.0 | >2.0 |
| 17 | >2.0 | 1.36 | >2.0 | <0.2 | <0.2 | >2.0 | — | — |
| 19 | >2.0 | >2.0 | >2.0 | <0.2 | <0.2 | >2.0 | — | — |
| 20 | >2.0 | >2.0 | >2.0 | >0.2 | 1.0 | >2.0 | — | — |
| 21 | >2.0 | >2.0 | >2.0 | 2.0 | 2.0 | 1.0 | — | — |
| 16 | 1.36 | 1.64 | 0.84 | 0.7 | 0.26 | 1.0 | >2.0 | 0.52 |

Table III

| | | Results of Pre-emergence Soil Application Herbicide Rate Evaluation Screen | | | | | | | |
|---|---|---|---|---|---|---|---|---|---|
| Example | Soil Type | Yellow-Foxtail | Fall-Panicum | Crab-grass | Pig weed | Wild Mustard | Velvet Leaf | Downey Brome | Barnyard Grass |
| 4 | Webster | >2.0 | <1.0 | >2.0 | <1.0 | <1.0 | 1.36 | >2.0 | 1.8 |
| | Hanford | 0.84 | 0.32 | >1.0 | 0.22 | 0.24 | 0.64 | 0.3 | 0.52 |
| 5 | Webster | >2.0 | 1.34 | >2.0 | <1.0 | <1.0 | 1.8 | >2.0 | >2.0 |
| | Hanford | 0.92 | 1.0 | >1.0 | 0.22 | <0.22 | 0.52 | 0.58 | 0.92 |

(The symbol < means "less than".)
(The symbol > means "greater than".)

In many instances the compounds of the invention possess a selective action against weeds in crop plant cultures. For example, control of grasses and broadleaf weeds in grain crops such as wheat can be achieved by post-emergence application of such compounds of the invention as:

4'-(sec-butoxy)-3'-(trifluoromethyl)-1-methylcyclopropanecarboxanilide,
4'-(isobutoxy)-3'-(trifluoromethyl-1-methylcyclopropanecarboxanilide.

The above species and/or other species of the invention have likewise shown post-emergence, and in some cases, pre-emergence selective activity for peanuts, grain sorghum, cotton, rice, corn, alfalfa or the like.

We claim:
1. A compound of formula I

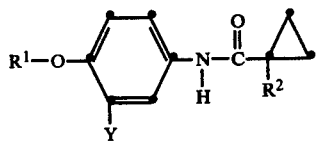

(I)

wherein
Y is $CF_3$;
$R^1$ is methyl, ethyl, isopropyl or cyclopropylmethyl; and
$R^2$ is a methyl group.

2. A compound according to claim 1 wherein $R^1$ is ethyl, or isopropyl.

3. A compound of the formula

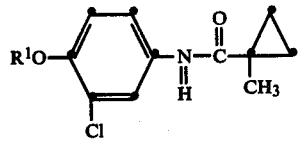

wherein
$R^1$ is isopropyl or 1-cyclopropylethyl.

4. A compound according to claim 3 wherein $R^1$ is 1-cyclopropylethyl.

5. A herbicidal composition comprising a herbicidally effective amount of a compound according to claim 1 and at least one surface-active agent or carrier.

6. A method for controlling undesirable plant growth at a locus to be protected which comprises applying to the locus to be protected a herbicidally effective amount of a compound according to claim 1 or a composition thereof.

7. A herbicidal composition comprising a herbicidally effective amount of a compound according to claim 3 and at least one surface-active agent or carrier.

8. A method for controlling undesirable plant growth at a locus to be protected which comprises applying to the locus to be protected a herbicidally effective amount of a compound according to claim 3 or a composition thereof.

* * * * *